(12) United States Patent
Papadimitriou et al.

(10) Patent No.: US 9,322,763 B2
(45) Date of Patent: Apr. 26, 2016

(54) AUTONOMOUS NON-DESTRUCTIVE INSPECTION

(71) Applicants: Stylianos Papadimitriou, Houston, TX (US); Wanda Papadimitirou, Houston, TX (US)

(72) Inventors: Stylianos Papadimitriou, Houston, TX (US); Wanda Papadimitirou, Houston, TX (US)

(*) Notice: Subject to any disclaimer, the term of this patent is extended or adjusted under 35 U.S.C. 154(b) by 0 days.

(21) Appl. No.: 14/095,085

(22) Filed: Dec. 3, 2013

(65) Prior Publication Data

US 2014/0107947 A1    Apr. 17, 2014

Related U.S. Application Data

(60) Continuation-in-part of application No. 13/304,136, filed on Nov. 23, 2011, now Pat. No. 8,831,894, which is a continuation-in-part of application No. 11/769,216, filed on Jun. 27, 2007, now Pat. No. 8,086,425, and a division of application No. 11/772,357, filed on Jul. 2, 2007, now Pat. No. 8,050,874, which is a continuation-in-part of application No. 10/867,004, filed on Jun. 14, 2004, now Pat. No. 7,240,010, and a continuation-in-part of application No. 11/769,216, filed on Jun. 27, 2007, now Pat. No. 8,086,425, which is a continuation-in-part of application No. 11/743,550, filed on May 2, 2007, now Pat. No. 7,403,871, and a continuation-in-part of application No. 10/867,004, filed on Jun. 14, 2004, now Pat. No. 7,240,010, said application No. 11/743,550 is a continuation-in-part of application No. 11/079,745, filed on Mar. 14, 2005, now Pat. No. 7,231,320, which is a continuation-in-part of application No. 10/995,692, filed on Nov. 22, 2004, now Pat. No. 7,155,369.

(51) Int. Cl.
| | |
|---|---|
| G01M 5/00 | (2006.01) |
| G01B 5/00 | (2006.01) |
| G01N 19/00 | (2006.01) |
| G01B 5/14 | (2006.01) |
| G10L 15/22 | (2006.01) |

(52) U.S. Cl.
CPC ............ G01N 19/00 (2013.01); G01B 5/00 (2013.01); G01B 5/14 (2013.01); G01M 5/0033 (2013.01); G10L 15/22 (2013.01)

(58) Field of Classification Search
CPC .................................................... G01M 5/0033
USPC ............................................................ 702/34
See application file for complete search history.

(56) References Cited

U.S. PATENT DOCUMENTS

| | | |
|---|---|---|
| 1,823,810 A | 9/1931 | Wall |
| 2,194,229 A | 3/1940 | Johnston et al. |

(Continued)

OTHER PUBLICATIONS

Papadimitriou, Steve et al, "The Inspection of Used Coil Tubing", Second International Conference and Exhibition on Coiled Tubing Technology, Adams Mark Hotel, Houston, Texas, Mar. 28-31, 1994.

*Primary Examiner* — Bryan Bui
(74) *Attorney, Agent, or Firm* — Kenneth L. Nash

(57) ABSTRACT

Autonomous non-destructive inspection equipment provides automatic and/or continuous inspection and evaluation of a material under inspection. The inspection equipment comprises at least one detection sensor and at least one detection sensor interface for a computer. The signals are communicated from the sensor to the computer. The signals are then conditioned and evaluated according to knowledge already inputted into the computer. The computer iterations are processed until an acceptable conclusion is made regarding the type of imperfection that is detected.

63 Claims, 7 Drawing Sheets

(56) References Cited

U.S. PATENT DOCUMENTS

| | | |
|---|---|---|
| 2,317,721 A | 4/1943 | Barnes |
| 2,527,000 A | 10/1950 | Drake |
| 2,582,437 A | 1/1952 | Jezeweski et al. |
| 2,685,672 A | 1/1954 | Price et al. |
| 2,770,773 A | 11/1956 | Cooley |
| 2,881,386 A | 4/1959 | Price et al. |
| 2,927,321 A | 3/1960 | Harris |
| 3,202,914 A | 8/1965 | Deem et al. |
| 3,225,293 A | 12/1965 | Wood et al. |
| 3,238,448 A | 3/1966 | Wood et al. |
| 4,523,468 A | 6/1985 | Derkacs et al. |
| 4,629,985 A | 12/1986 | Papadimitriou et al. |
| 4,698,631 A | 10/1987 | Kelly, Jr. et al. |
| 4,710,712 A | 12/1987 | Bradfield et al. |
| 4,821,575 A | 4/1989 | Fujikake et al. |
| 4,825,385 A | 4/1989 | Dolph et al. |
| 5,202,680 A | 4/1993 | Savage |
| 5,210,704 A | 5/1993 | Husselny |
| 5,321,362 A | 6/1994 | Fischer et al. |
| 5,371,462 A | 12/1994 | Hedengren et al. |
| 5,430,376 A | 7/1995 | Vierti |
| 5,440,237 A | 8/1995 | Brown et al. |
| 5,455,777 A | 10/1995 | Fujiyama et al. |
| 5,648,613 A | 7/1997 | Kiefer |
| 5,671,155 A | 9/1997 | Edens et al. |
| 5,774,378 A | 6/1998 | Yang |
| 5,777,891 A | 7/1998 | Pagano et al. |
| 5,786,768 A | 7/1998 | Chan et al. |
| 5,914,596 A | 6/1999 | Weinbaum |
| 5,943,632 A | 8/1999 | Edens et al. |
| 5,970,438 A | 10/1999 | Clark et al. |
| 6,115,674 A | 9/2000 | Brudnoy et al. |
| 6,279,125 B1 | 8/2001 | Klein |
| 6,359,434 B1 | 3/2002 | Winslow et al. |
| 6,378,387 B1 | 4/2002 | Froom |
| 6,480,811 B2 | 11/2002 | Denny et al. |
| 6,560,555 B1 | 5/2003 | Mallory |
| 6,580,268 B2 | 6/2003 | Wolodko |
| 6,594,591 B2 | 7/2003 | Clark et al. |
| 6,697,466 B2 | 2/2004 | Howard et al. |
| 6,727,691 B2 | 4/2004 | Goldfine et al. |
| 6,784,662 B2 | 8/2004 | Schlicker et al. |
| 6,836,560 B2 | 12/2004 | Emery |
| 6,847,207 B1 | 1/2005 | Veach et al. |
| 6,904,818 B2 | 6/2005 | Harthorn et al. |
| 6,975,108 B2 | 12/2005 | Bilik et al. |
| 7,082,822 B2 | 8/2006 | Harthorn et al. |
| 7,104,125 B2 | 9/2006 | Harthorn et al. |
| 7,155,369 B2 | 12/2006 | Papadimitriou et al. |
| 7,159,654 B2 | 1/2007 | Ellison et al. |
| 7,231,320 B2 | 6/2007 | Papadimitriou et al. |
| 7,240,010 B2 | 7/2007 | Papadimitriou et al. |
| 7,403,871 B2 | 7/2008 | Papadimitriou et al. |
| 8,050,874 B2 | 11/2011 | Papadimitriou et al. |
| 8,086,425 B2 | 12/2011 | Papadimitriou et al. |
| 8,428,910 B2 | 4/2013 | Papadimitriou et al. |
| 2003/0139916 A1* | 7/2003 | Choe et al. ............... 703/10 |
| 2003/0229476 A1 | 12/2003 | Naganarayana et al. |
| 2004/0225474 A1 | 11/2004 | Goldfine et al. |
| 2005/0127908 A1 | 6/2005 | Schlicker et al. |
| 2006/0096105 A1* | 5/2006 | Haugland ............... 33/304 |
| 2013/0060487 A1 | 3/2013 | Papadimitriou et al. |

\* cited by examiner $$Ya_{ij} = M \sum_{k=1}^{N} a_{ik} Xa_{kj} \qquad \text{(Equation 1)}$$

$$Ya_{ij} = T_{\left(M \sum_{k=1}^{N} a_{ik} Xa_{kj}\right)} \qquad \text{(Equation 2)}$$

$$Ya_{ij} = M \left[ 1 + e^{-\sum_{k=1}^{N} a_{ik} Xa_{kj}} \right]^{-1} \qquad \text{(Equation 3)}$$

Fig. 2B

1. The Riser is transferred from the Rig onto a Workboat for transport to shore – incurring downtime, risking handling & transportation damage and polluting the environment.

2. The Riser is transferred from the Workboat onto a Truck for transport to the inspection facility – risking handling & transportation damage and polluting the environment.

3. At the inspection facility the Riser is unloaded from the truck - risking handling damage.

4. At the inspection facility the Riser is disassembled – risking handling damage, disassembly damage, damaging and misplacing parts, errors and omissions.

5. At the inspection facility the Riser is pressure washed – polluting the environment.

6. At the inspection facility the Riser paint/coating is removed – polluting the environment.

7. \The Riser undergoes inspection leaving more than 95% of the Riser condition unknown.

8. At the inspection facility the Riser is painted/coated – polluting the environment.

9. At the inspection facility the Riser is re-assembled – risking handling damage and assembly errors and omissions.

10. At the inspection facility the Riser is loaded onto a Truck for transport to a Workboat - risking handling & transportation damage and polluting the environment..

11. The Riser is transferred from the Truck onto a Workboat for transport to the Rig – risking handling & transportation damage and polluting the environment.

12. The Riser is transferred from the Workboat onto a Rig – risking handling damage.

There is a high probability that the Riser comes back onto the Rig in worst condition than when it was send onshore for the Inspection.

Fig. 4

Riser Inspection at the onshore inspection facility

1. Visual inspection - *a subsea engineer should perform this step on every Riser trip, not once every 5 years.*

2. Dimensional inspection - *a subsea engineer should perform this step with automatic pass-fail tools on every Riser trip, not once every 5 years.*

3. Riser Inspection of Main Tube and Auxiliary Lines – *comprises of a few spot wall thickness readings resulting in less than 1% inspection coverage. It should be noted that fence posts and driveway culvert pipes are inspected with a higher standard.*

4. Weld inspection - *Magnetic Particle inspection is limited to surface and near-surface Imperfections; it does not scan the weld volume. TOFD inspection dead-zones limit the usefulness of TOFD.*

5. Liquid Penetrant of surfaces.

Fig. 5

Calculation of Riser Inspection Coverage at the onshore inspection facility

A 75' (900") Length x 21"OD Riser Main Tube will be used in the following example.

The OD Circumference is:  [21.0" * π] = 65.97"  (66.0")

Good-Quality NDI requires a 20% sensor overlap per reading. Typical <u>Ultrasonic</u> and <u>Eddy-Current</u> Sensor diameter = 0.50" resulting in one reading per 0.4" step.

Lengthwise readings for 100% MT coverage:  [900" / 0.4"] = 2,250

Circumferential readings for 100% coverage:  [66" / 0.4"] = 165

Total Number of MT 100% coverage readings: [2,250 * 165] = 371,250

Taking four (4) readings every 2' (24.0") results in [38 * 4] = 152 total readings, for a coverage of [152 / 371,250] = 0.04% leaving 99.96% of the MT not inspected.

The above example may easily be recalculated using different inspection sensor sizes and different number of readings.

Fig. 6

AUTONOMOUS NON-DESTRUCTIVE INSPECTION

RELATED APPLICATIONS

This application is a continuation in part of U.S. patent application Ser. No. 13/304,136 having a filing date of Nov. 23, 2011, now U.S. Pat. No. 8,831,894, which is a division of U.S. patent application Ser. No. 11/772,357 having a filing date of Jul. 2, 2007, now U.S. Pat. No. 8,050,874, which is a continuation in part of U.S. patent application Ser. No. 10/867,004 having a filing date of Jun. 14, 2004, now U.S. Pat. No. 7,240,010, U.S. patent application Ser. No. 13/304,136 having a filing date of Nov. 23, 2011, now U.S. Pat. No. 8,831,894, is also a continuation in part of U.S. patent application Ser. No. 11/769,216 having a filing date of Jun. 27, 2007, now U.S. Pat. No. 8,086,425, which is a continuation in part of U.S. patent application Ser. No. 11/743,550 having a filing date of May 2, 2007, now U.S. Pat. No. 7,403,871, which is a continuation of U.S. patent application Ser. No. 11/079,745 having a filing date of Mar. 14, 2005, now U.S. Pat. No. 7,231,320, which is a continuation in part of U.S. patent application Ser. No. 10/995,692 having a filing date of Nov. 22, 2004, now U.S. Pat. No. 7,155,369.

U.S. patent application Ser. No. 11/772,357 having a filing date of Jul. 2, 2007, now U.S. Pat. No. 8,050,874, is also a continuation in part of U.S. patent application Ser. No. 11/769,216 having a filing date of Jun. 27, 2007, now U.S. Pat. No. 8,086,425, which is also a continuation in part of U.S. patent application Ser. No. 10/867,004 having a filing date of Jun. 14, 2004, now U.S. Pat. No. 7,240,010.

Each and every patent and application listed above is hereby incorporated by reference.

BACKGROUND OF THE INVENTION

1. Field of the Invention

This invention relates, generally, to non-destructive inspection and inspection equipment, and more specifically, to provide automatic and/or continuous non-destructive inspection and evaluation to material under inspection, including evaluators and predictors of detected imperfections and useful material life.

2. Description of the Prior Art

As is known in the art, materials are selected for use based on criteria including minimum strength requirements, useable life, and anticipated normal wear. Safety factors are typically factored into design considerations to supplement material selection in order to aid in reducing the risk of failures including catastrophic failures. Such failures may occur when the required application strengths exceed the actual material strength. During its useful life, material deteriorates and/or is weakened by external events such as mechanical and/or chemical actions arising from the type of application, repeated usage, hurricanes, earthquakes, storage, transportation, and the like; thus, raising safety, operational, functionality, and serviceability issues requiring the determination of the material remaining strength for the type of application.

The non-destructive-inspection industry (herein after referred to as "NDI") has utilized a variety of techniques and devices with the majority based on the well known and well documented techniques of audible, color, dimensional, dye penetrant, eddy-current, emat, magnetic flux leakage, laser, magnetic particle, radiation, such as x-ray and gamma ray, sound, ultrasonic and visual techniques. These techniques have been utilized alone or in combination with each other to address the specifics of the Material-Under-Inspection (herein after referred to as "MUI"). A list of typical MUI includes, but is not limited to, aircraft, bridges, cranes, drilling rigs, frames, chemical plant components, engine components, risers and riser components, oil country tubular goods (herein after referred to as "OCTG" or "tubular goods"), pipelines, power plant components, rails, refineries, rolling stoke, sea going vessels, service rigs, structures, vessels, workover rigs, other components of the above, combinations of the above, and similar items.

Typical NDI devices deploy a single sensor per material area and are therefore classified as one-dimensional (herein after referred to as "1D-NDI"). 1D-NDI comingles all MUI signals into one sensor signal, thus it does not permit for the solution of a system of equations that describes MUI and significantly limits the 1D-NDI dynamic range. Because of the signal comingling and the limited dynamic range, 1D-NDI cannot detect many of the dangerous imperfections early on, such as fatigue, and has a limited operational range for pipe size, configuration, wall thickness, types of imperfections, inspection speed, sampling rate and similar items while it still relies on the manual intervention of a verification-crew to locate and identify the source of the 1D-NDI signal. Instead of an affirmative verification that MUI exceeds the minimum strength requirements for the application, NDI is carried out with the aid of a manual verification crew, to determine that the few imperfections within the NDI detection capabilities are not present. Thus, the NDI limitations govern the inspection process and outcome, not MUI needs, the application needs or the safety needs.

In addition, NDI dictates termination of MUI utilization altogether in order to accommodate the inspection process, which, is typically carried out by shipping MUI to an inspection facility (illustrated in FIG. 4), regardless if it needs inspection or maintenance, because NDI cannot determine the need onsite and the NDI data cannot be used to calculate a remaining strength or the next inspection interval. Furthermore, NDI imposes, at minimum, cleaning of MUI, removal of paint or coating and other similar restrictions; thus, NDI is, at minimum, an intrusive process. When MUI paint or coating is removed, NDI is a destructive process. NDI would be non-destructive if it inspects MUI without removing the paint or coating. And non-intrusive if inspects MUI where-is as-is. Again, NDI cannot detect imperfections early on. Instead, NDI focuses on end-of-life imperfections where deterioration is accelerated significantly and which are detectable by a manual verification crew.

For complex OCTG, such as a marine drilling riser (herein after referred to as "Riser"), illustrated as item 71 in FIG. 3, this process also requires the removal of buoyancy; cleaning; disassembly; removal of paint or coating (illustrated in FIG. 4); performing a very limited 1D-NDI comprising of a few spot-checks that typically results in less than 1% inspection coverage (illustrated in FIG. 5, 6); re-painting or re-coating; re-assembly; installation of the buoyancy and shipping back to the rig with about 99% of Riser condition still unknown. The cost of inspection is therefore increased by the transportation and handling cost along with the material downtime. In addition, assembly errors and omissions along with the shipping and handling, especially after the inspection, may induce damage to Riser that could result in an unanticipated early catastrophic failure.

Because of its implementation and the intrusion NDI limitations impose, typical inspections have been expensive and thus are performed at rare intervals or not performed at all. Risers, for example, are shipped to shore for inspection on a five year cycle, with 20% of Risers inspected per year, in a process that provides insignificant inspection coverage but may be harmful, especially for Risers that do not need any maintenance. In addition, NDI costs can be as high as 30% of the OCTG replacement cost.

SUMMARY OF THE INVENTION

The novel autonomous inspection system, control, and method (herein after referred to as "AutoNDI") that are presented hereinbelow can be used as an "advisor" to an inspector in one embodiment. In another embodiment, AutoNDI can be used as a standalone low-cost inspection system, preferably at MUI deployment site to perform a non-destructive and preferably non-intrusive inspection of the as-is MUI. As a standalone system, the AutoNDI can bring the cost of inspection down due to its non-intrusive implementation and on-going inspection. The non-intrusiveness allows for the inspection to be carried out, in many applications, while MUI is in operation and without requiring the operation to stop (such as when tripping OCTG into or out of a well). Further, because of the nature of the constant inspection, major defects are more likely to be found and minor defects can be better monitored over time to predict the useable life of MUI.

In yet another possible embodiment, an AutoNDI may be provided to ascertain and/or to mitigate hazards arising from the exploration, production, transportation and processing of hydrocarbons, onshore or offshore, trough constant-vigilance. For example, on an offshore drilling rig, illustrated as item 70 on FIG. 3, an AutoNDI may scan Risers and then scan the drill pipe or any other OCTG, including but not limited to casing, coiled tubing, pipeline, tubing, bottom hole assembly and other equipment on every trip thereafter. It may also be deployed to scan the lifting and tensioner cables, wireline, BOP, the derrick, the crane and other rig structural members, components and equipment. This constant-vigilance approach would greatly reduce the public, personnel, environment and equipment risk by detecting imperfections early enough, before they affect the usability of MUI.

In another possible embodiment, an AutoNDI may compare onsite the as-is Material status with stored previous scans to determine a deterioration and the rate of deterioration.

These and other embodiments, objectives, features, and advantages of the present invention will become apparent from the drawings, the descriptions given herein, and the appended claims. However, it should be understood that above-listed embodiments and/or objectives and/or advantages of the invention are intended only as an aid in quickly understanding certain possible aspects of the invention, are not intended to limit the invention in any way.

DESCRIPTION OF DRAWINGS

FIG. 2B illustrates the identifier equations of an autonomous non-destructive inspection system according to the present invention.

FIG. 4 illustrates the steps and hazards involved in the transport of Riser or any other OCTG from the rig to an onshore inspection facility and then back onto the rig.

FIG. 5 illustrates a Riser inspection process at the onshore inspection facility.

FIG. 6 illustrates a calculation of Riser inspection coverage at the onshore inspection facility.

DETAILED DESCRIPTION OF THE INVENTION

To understand the terms associated with the present invention, the following descriptions are set out hereinbelow. It should be appreciated that mere changes in terminology cannot render such terms as being outside the scope of the present invention.

Autonomous: able to function without external control or intervention.

Knowledge: a collection of facts and rules capturing the knowledge of one or more specialist.

Rules: how something should be done to implement the facts.

Imperfection: a discontinuity, irregularity, anomaly, inhomogeneity, or a rupture in the material under inspection.

Flaw: an imperfection that exceeds a specified alert threshold.

Defect: an imperfection that exceeds a specified threshold and may warrant rejection of the material under inspection.

Classification: assigning an imperfection to a particular class based on its features.

Figure 1:
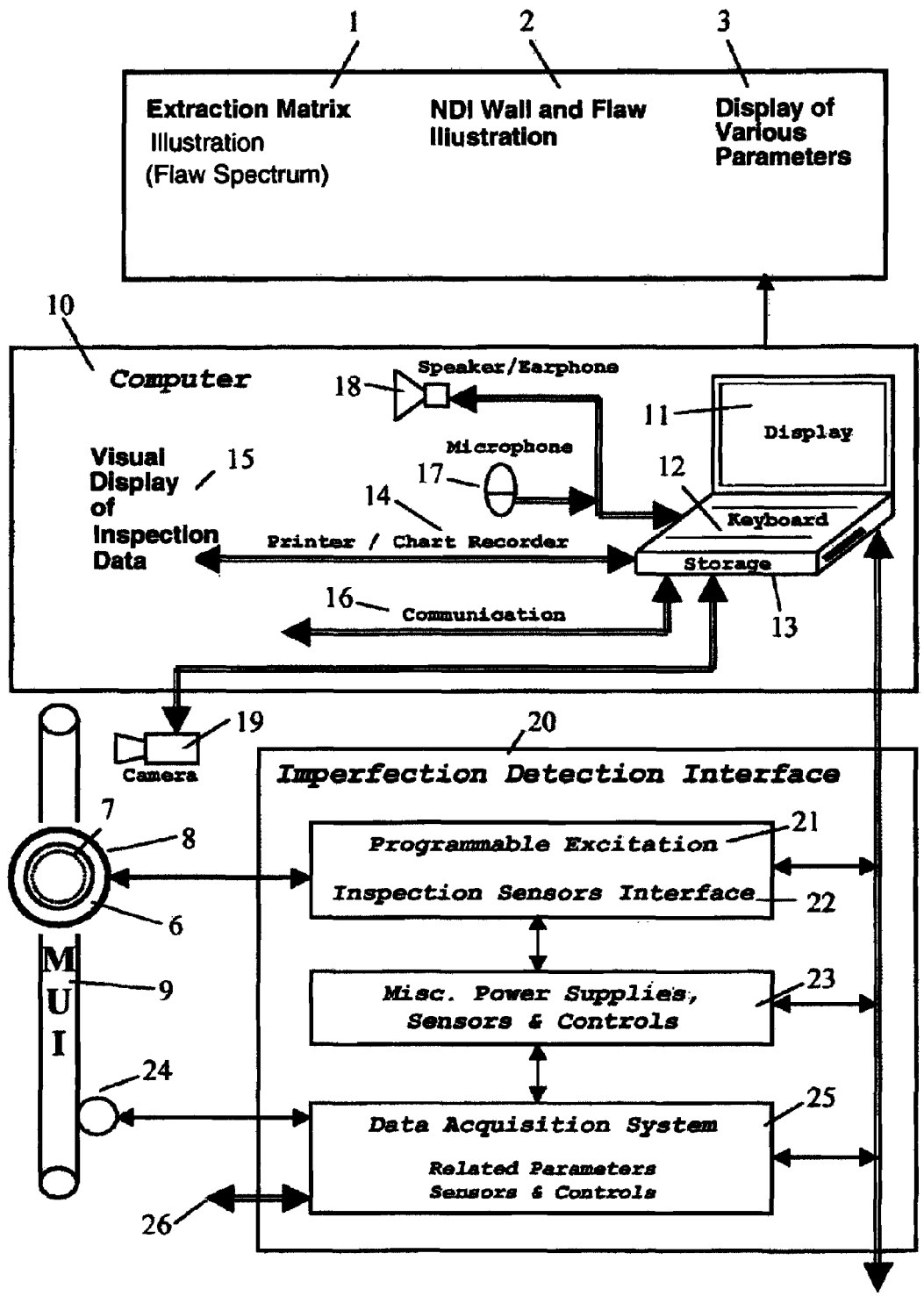
FIG. 1 illustrates a block diagram of an autonomous non-destructive inspection system according to the present invention.

FIG. 1 illustrates a block diagram of an AutoNDI further illustrating inspection computer 10, imperfection detection interface 20, and the preferable information exchange among the components of the inspection equipment. It should be understood that inspection computer 10 may consist of more than just one computer such as a cluster of interconnected computers. Computer 10 preferably comprises keyboard 12, display 11, storage capacity 13 for storing and accessing data, microphone 17, speaker 18 and camera 19. It should be understood that display 11, keyboard 12, microphone 17 and speaker 18 may be local to computer 10, may be remote, may be portable, or any combination thereof. It should be further understood that camera 19 may comprise more than one camera. Furthermore, camera 19 may utilize visible light, infrared light, any other spectrum component, or any combination thereof. Camera 19 may be used to relay an image that may be used for recognition and identification or a measurement such as a temperature measurement, a dimensional measurement, a comparative measurement, or any combination thereof. It should be appreciated that the stored data may comprise hard disks, floppy disks, compact discs, magnetic tapes, DVDs, memory, cloud and other storage devices. Computer 10 may transmit and receive data through at least one communication link 16 and may send data to printer or chart recorder 14 for further visual confirmation of inspection data 15 and other related information. Computer 10 preferably provides for data exchange with imperfection detection interface 20.

Regardless of the specific inspection technique utilized, AutoNDI will preferably scan the material after each use, fuse the inspection data with relevant material use parameters, and automatically determine the status of MUI 9. Thus, a function of imperfection detection interface 20 is to generate and induce excitation 21 into MUI 9 and detect the response of MUI 9 to programmable excitation 21. Preferably, at least one inspection head 8 is mounted on or inserted in MUI 9 and head 8 may be stationary or travel along MUI 9 in response to wave action for example. It should be appreciated that inspection head 8 can be applied to the inside as well as the outside of MUI 9. It should be understood that inspection head 8, illustrated herein, may comprise at least one excitation inducer 6 and one or more inspection sensors 7 mounted such that the inspection needs of MUI 9 are substantially covered. Inspection computer 10 preferably both programs and controls excitation 21 and inspection head 8, as well as receives data from inspection head sensors 7 through inspection sensor interface 22. Inspection head 8, excitation 21, and inspection sensor interface 22 may be combined within the same physical housing. In an alternative embodiment, inspection sensors 7 may comprise computer capability and memory storage and thus sensors 7 can be programmed to perform many of the tasks of computer 10 or perform functions in tandem with computer 10. It should be also understood that the application of excitation 21 and the inspection of MUI 9 may be delayed, such as NDI utilizing, for example, the residual magnetic field whereby MUI 9 is magnetized and it is inspected at a later time.

Computer 10 also controls and monitors a plurality of power supplies, sensors and controls 23 that facilitate the inspection process including but not limited to safety features. Further, computer 10 monitors/controls data acquisition system 25 which preferably assimilates data from at least one sensor 24. Sensor 24 preferably provides data such as, but not limited to, MUI 9 location, penetration rate, rate of rotation (rpm), coupling torque, similar items and combinations thereof. It should be appreciated that the data to be acquired will vary with the specific type of MUI 9 and thus the same parameters are not always measured and/or detected. Furthermore and in addition to the aforementioned inspection techniques, computer 10 may also monitor, through data acquisition system 25, parameters that are related to the inspection or utilization of MUI 9 through sensors and transducers 26 distributed around MUI 9 deployment area. For ease of understanding, these various sensors and transducers are designated with the numeral 26 and may monitor such characteristics as, but are not limited to, acoustic, barcode, chemical, color, conductivity, current, deformation, depth, direction, distance, eddy-current, electrical, emat, field, flow, flux-leakage, force, frequency, geometry, heave, height, laser, length, level, location, mean, motion, magnetic, optical, peak, physical properties, pitch, pressure (internal, external, wellhead), radiation, rate, reluctance, resistance, rig motion, roll, rpm, speed, stress, temperature, time, vibration, voltage, waves, weight, similar items and combinations thereof. One example of sensor 26 could be an RFID reader or a barcode scanner to identify MUI 9. Camera 19 may also be used to identify MUI 9. At least one other sensor could measure the response of the floating platform to the waves and the resulting motion of inspection head 8 in reference to the sea floor. Further, such parameters may be displayed in a manner illustrated by element 3 in FIG. 1. The STYLWAN Rig Data Integration System (RDIS-10) is an example of such an inspection system (STYLWAN is a trade mark of STYLWAN, Incorporated).

Signal Processing

Preferably, inspection head 8 relates time-varying continuous (analog) signals, such as, but not limited to, echo, field, reluctance, resistance, impedance, absorption, attenuation, or physical parameters that may or may not represent an imperfection of MUI 9. It should be appreciated by those in the art that sensor 7 signals generally include, but are not limited to, noise and useable data that may indicate some imperfection and/or defect. Further, imperfections generally comprise all received signals and may include MUI 9 design features such as tapers, major and minor imperfections, flaws, defects or other MUI 9 conditions such as surface roughness, hardness, composition changes, geometry, scale, dirt, and the like. Typically, those in the art have always relied on both an inspector and a manual verification crew for the interpretation of the inspection signals, referred to as a flag, and any subsequent disposition of MUI 9. However, based on extensive strength-of-materials knowledge, it is well known that the severity of an MUI 9 imperfection is a function of its geometry, its location, the material composition, hardness, geometry and the applied loads. It is also well known, in the art, that this information cannot be readily obtained by a verification crew when the imperfections in question are located underneath paint or coating, in the near subsurface, in the mid wall, or in the internal surface of MUI 9. Any destructive action, such as removing any paint or coating or cutting up MUI 9 is beyond the scope of non-destructive inspection. In addition, disassembly, such as illustrated in FIG. 4, does not conform to non-intrusive-inspection principles.

Again, 1D-NDI flags a location for a verification crew. Where pipelines are concerned, verification means: travel to a location, dig up the pipeline, perform a limited visual and ultrasonic inspection and remediate the area. It is not uncommon to verify hundreds of locations over a period of months but miss entirely the location in need of maintenance due to 1D-NDI commingling of the signals and it limited dynamic range.

Detailed signal analysis can extract the pertinent information from the NDI signals. Preferably, such detailed signal analysis would utilize signals that are continuously related in form, kind, space, and time. The signals are preferably band limited and are converted to time-varying discrete digital signals which are further processed, by computer 10, utilizing an extraction matrix to decompose the signals and extract relevant features in a manner illustrated by element 1 in FIG. 1. The extraction matrix is compiled through a software program, that was published in 1994 and it is beyond the scope of this patent. The extraction matrix decomposes the converted digital signals into relevant features. The extraction matrix may be adjusted to decompose the signals into as few as two (2) features, such as, but not limited to, the classical 1D-NDI presentation of wall and flaw in a manner illustrated by element 2 in FIG. 1. It should be understood that no theoretical decomposition upper limit exists; however, ten (10) to two hundred (200) features are practical. The selection of the identifier equations, further described herein below, typically sets the number of features. In the exemplary RDIS-10, the decomposed signals are known as flaw spectrum 1.

Pattern Recognition

Humans are highly adept in recognizing patterns, such as facial features or flaw spectrum 1 and readily correlating any pertinent information. Therefore, it is easy for the inspector to draw conclusions about MUI 9 by examining flaw spectrum 1. During the inspection, the inspector further incorporates his/her knowledge about MUI 9 present status, his/her observations, as well as the results of previous inspections. The success of this inspection strategy of course, solely depends on how well the inspector understands flaw spectrum 1 data and the nuances it may encompass.

Computers on the other hand, can run numerical calculations rapidly but have no inherent pattern recognition or correlation abilities. Flaw Spectrum 1 recognition requires high-accuracy and fast-processing (short recognition time). Thus, a program has been developed that preferably derives at least one mathematical procedure to enable computer 10 to automatically recognize the patterns and nuances encompassed in decomposed inspection data streams such as presented in flaw spectrum 1. It should be noted that multi-stage feature extraction outperforms single-stage feature extraction up to a certain complexity beyond which performance declines. The detailed mathematical procedures described hereinbelow enable one skilled in the art to implement the AutoNDI described herein without undue experimentation.

Figure 2A:
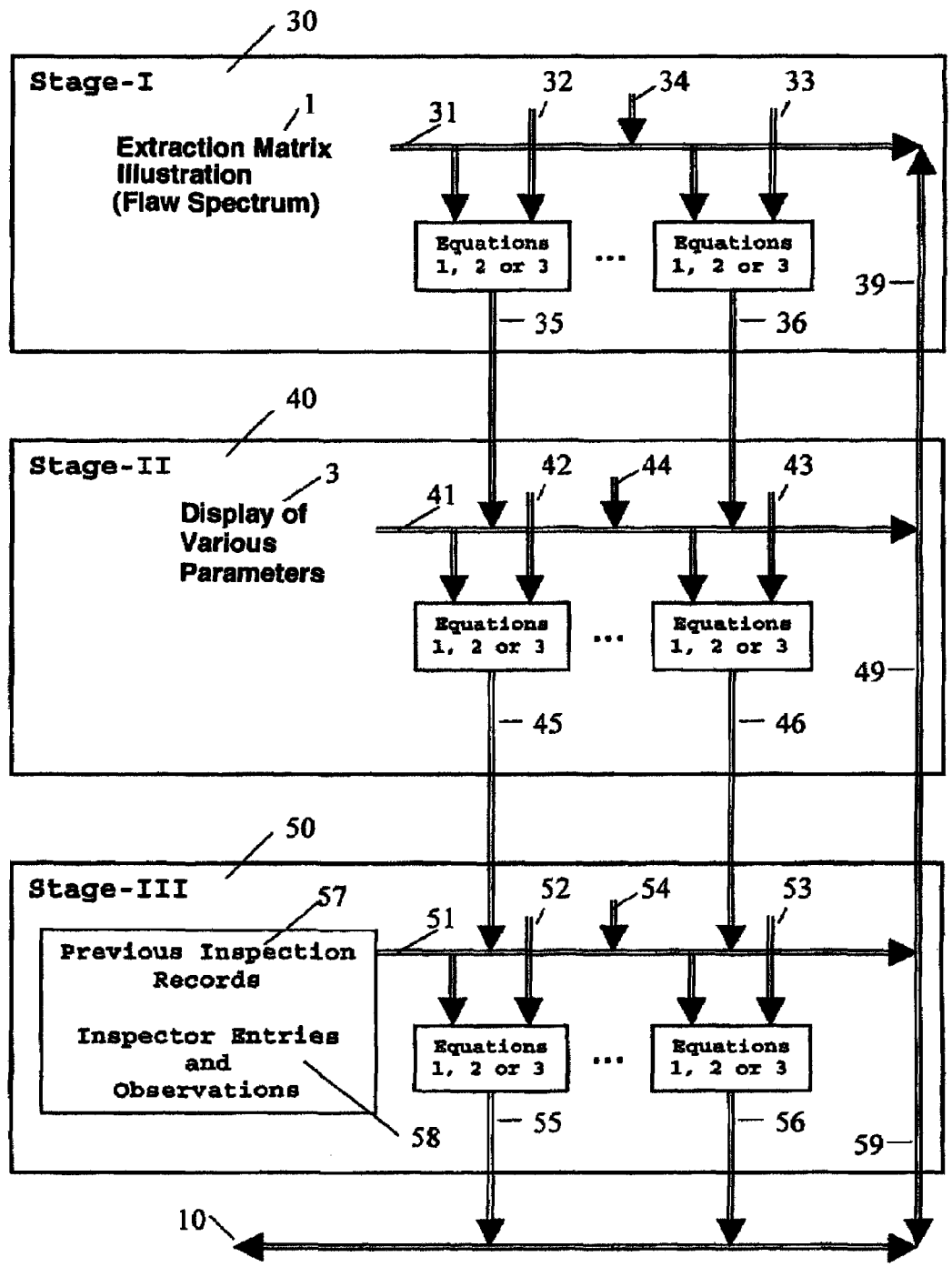
FIG. 2A illustrates a block diagram of the signal processing of an autonomous non-destructive inspection system according to the present invention.

FIG. 2A illustrates a block diagram of an inspection data processing sequence that allows the creation of a software flowchart and the translation of the practice to a computer program. For stand-alone operation, the AutoNDI must be optimal in regard to the inspection criteria and application limitations, commonly defined by approximations and probabilities which are referred to herein as constraints. It should be understood therefore, that the AutoNDI state variables must be tuned for optimal performance under different constraints depending on MUI 9 and its application. The fundamental operation of the AutoNDI is performed by the identifier equations which preferably capture the optimal mutual features in accordance to the constraints. The AutoNDI identifier equations are illustrated in FIG. 2B. It should be understood that additional identifier equations may be utilized and that a number of identifier equations may be paralleled and/or cascaded, each one utilizing a different set of optimal mutual features. Furthermore, it should be understood that the processing of the identifier equations may be carried out by a single computer 10 or by different computers in a cluster without affecting the overall result.

Stage-I 30 identifier equations used for input features 31 are mostly derived from flaw spectrum 1. Additional features may be provided by fixed values referred to herein as bias 34, 44, 54. Bias may be a single constant or a sequence of constants that may be controlled, but not limited, by time or by MUI 9 length. Backwards chaining 39 limits irrelevant processing and enhances stability while forward chaining 59 propagates features to later stages or it may inform computer 10 that an MUI 9 condition has been determined and no further analysis is required. It should be further understood that both forward and backward chaining may be direct, through memory, through a bucket-brigade (time delay or length delay), or any combination of the above.

It should be further understood that all or any subsystem of the AutoNDI may be implemented as a casual system or as a non-casual system. In a casual implementation only past and present features 31 are utilized. In a non-casual implementation, features 31 are utilized through memory, through a bucket-brigade, or any combination of the above thus allowing for the use of future values of features 31. Future values of features 31 may be used directly or indirectly as signal masks and may be propagated through the forward chaining 59. Utilization of future values of features 31 increases the AutoNDI stability and reduces the probability of a conflict. Equations 1, 2 or 3 reduce features 31 and bias 34 to identifiers 35, 36 denoted as Ya in FIG. 2B.

Identifiers Ya 35, 36 can be fed back through the backwards chaining 39, can be used directly through the forward chaining 59, can be used as variables to equations or as features 41, 51 in following stages or in their most practical form, as indexes to tables (arrays) which is shown in FIG. 2B Equation 2 for clarity. Another useful identifier form is shown in FIG. 2B Equation 3 where M is a scaling constant or function.

It should be understood that each stage may comprise multiple identifier equations utilizing equations 1, 2, 3, other crisp or fuzzy equations, similar items and combinations thereof. There is no theoretical upper limit for the number of identifiers calculated; however, five (5) to ten (10) identifiers are practical.

Some of identifiers Ya 35, 36 may be sufficient to define the disposition of MUI 9 alone and thus propagate to the output stage 59 while others may become features for the second stage 40 of identifier equations along with features 41 pertinent to the Ya identifiers. It should be appreciated that in the exemplary STYLWAN RDIS-10, depending on the constraints, those features can be obtained from the operator interface, from computer 10 memory, from camera 19, or by connecting directly to the STYLWAN RDIS-10 Data Acquisition System transmitters that measure various parameters illustrated FIG. 1 (3). (STYLWAN is a trademark of STYLWAN, Incorporated). The second stage 40 identifier equations produces identifiers 45, 46 of similar form as Ya identifiers 35, 36. It should be understood that this process may repeat until an acceptable solution to the constraints is obtained, however, three stages are typically adequate for the exemplary RDIS-10.

For the determination of the coefficients $a_{i,k}$, illustrated as 32 and 33 (similarly for 42, 43, 52, 53), a set of flaw spectrums 1 of known similar imperfections that are pertinent to a current inspection application are required. These data sets of flaw spectrums 1, are referred to herein as "Baseline Spectrums". Preferably, all the coefficients $a_{i,k}$, are initially set equal. It should be understood that because this is an iterative process the initial values of the coefficients $a_{i,k}$ could also be set by a random number generator, by an educated guess, or by other means for value setting.

Since the Baseline Spectrums are well known, typically comprising data taken for similar imperfections, the performance measure and the constraints are clearly evident and the coefficients solution is therefore objective, although the selection of the imperfections may be subjective. By altering the coefficient values through an iterative process while monitoring the output error an acceptable solution would be obtained.

There are multiple well-known techniques to minimize the error and most of these techniques are well adept for computer use. It should be appreciated that for the limited number of features, a trial-and-error brute force solution is feasible with the available AutoNDI computer power. It should be further expected that different solutions would be obtained for every starting set of coefficients. Each solution is then evaluated across a variety of flaw spectrums 1, referred to herein as "Validation Spectrums", as each solution has its own unique characteristics. It is imperative, therefore, that an extensive library of both Baseline Spectrums and Validation Spectrums must be available for this evaluation. It should be further understood that the Baseline Spectrums cannot be used as Validation Spectrums and vice versa. Furthermore, it should be understood that more than one solution may be retained and used for redundancy, conflict resolution, and system stability. Still further in applications of the AutoNDI, the terms "acceptable" or "good enough" are terms of art to indicate that, in a computational manner, the computer has completed an adequate number of iterations to compile an answer/solution with a high probability of accuracy. Good enough is also a solution to a fuzzy problem.

Once a set or sets of coefficients are obtained, the number of non-zero coefficients is preferably minimized in order to improve computational efficiency. This is important because each identifier equation is just a subsystem and even minor inefficiencies at the subsystem level could affect the overall system real time performance significantly. Multiple techniques can be used to minimize the number of non-zero coefficients. A hard threshold would set all coefficients below a predetermined set point to zero (0). Computers typically have a calculation quota, so a quota threshold would set to zero a sufficient number of lower value coefficients to meet the calculation quota. A soft threshold would subtract a non-zero constant from all coefficients and replace the negative values with zero (0). Since an error measure exists, the new set of coefficients can be evaluated, the identifier equations can be tuned again and the process could repeat until the admissible identifier equation is determined. It is preferred that multiple admissible identifier equations are determined for further use. It should be appreciated that although the preference for multiple admissible identifiers may appear to complicate potential resolutions, the use of computer power makes a large number of iterations feasible.

For the inspection of materials, an acceptable solution would always contain statistics based on false-positive and false-negative ratios. A false-positive classification rejects good material while a false-negative classification accepts defective material. Using more than one identifier equation lowers the false ratios more than the fine-tuning of a single identifier equation. It should be understood that this process theoretically provides an infinite number of solutions, as an exact formulation of the inspection problem is elusive and always based on constraints. Furthermore, for a solution that can be obtained with a set of coefficients, yet another solution that meets the performance measure may also be obtained by slightly adjusting some of the coefficients. However, within the first three to five proper iterations the useful solutions become obvious and gains from additional iterations are mostly insignificant and hard to justify.

Once all of Stage-I 30 admissible identifier equations have been determined, their identifiers become features in Stage-II 40 along with the additional features 41, bias 44, and forward and backwards chaining 49. The starting set of baseline spectrums is then processed through the admissible identifier equations and the results are used to tune Stage-II 40 identifier equations in a substantially identical process as the one described above for Stage-I 30. The process repeats for Stage-III 50 identifier equations and any other stages (not illustrated) that may be desired or necessary until all the admissible subsystems are determined and the overall system design is completed. It should be appreciated that in practice, preferably only two to five stages will be necessary to obtain required results. It should further be appreciated that different number of stages may be utilized for the different Features. When the final coefficients for all of the equations are established, the overall system performance may be improved by further simplifying the equations using standard mathematical techniques.

Incorporating Historical Data

A previous inspection, preferably with the same equipment, provides the best historical data 57. The previous inspection system output is ideally suited for use as feature 51 in the current inspection as it was derived from substantially the same constraints. Furthermore, more than one previous inspection 57 may be utilized. Features 51 may be backwards chained 49, 39. Multiple historical values may allow for predictions of the future state of the material and/or the establishment of a service and maintenance plan.

In conventional inspection systems, previous state data, which was derived through different means under different constraints, could not necessarily be used directly or used at all. If utilized, the data would more likely have to be translated to fit the constraints of the current application. It should be appreciated that such a task may be very tedious and provide comparatively little payoff. For example, there is no known process to translate an X-Ray film into Magnetic-Flux-Leakage (MFL) pertinent data. However, the system described herein allows for the use of such data in a simple and direct form. In the X-Ray example, the opinion of an X-Ray specialist may be solicited regarding the previous state of the material. The specialist may grade the previous state of the material, for example, in the range of one (1) to ten (10), with one (1) meaning undamaged new material. The X-Ray specialist opinion is an example of bias 34, 44, 54.

Bias 34, 44, 54 may not necessarily be derived in its entirety from the same source nor be fixed throughout the length of the material. For example, information from X-Rays may be used to establish the previous material status for the first 2,000 feet of an 11,000 foot coiled tubing string. Running-feet may be used to establish the previous material status for the remainder of the string except the 6,000 foot to 8,000 foot range where OD corrosion has been observed by inspector 58. From the available information, the previous material status for this string (bias per 1,000 feet') may look like [2, 2, 4, 4, 4, 4, 7, 7, 4, 4, 4] based on length. Other constraints though may impose a hard threshold to reduce the bias into a single value, namely [7], for the entire string.

An example of a bias array would be a Riser string where each riser joint is assigned a bias based on its age, historical use, Kips, vortex induced vibration, operation in loop currents, visual inspection, fatigue and the like. The bias for a single riser joint may then look like [1, 1, 3, 0, 2, 2]. Identifier equations may also be used to reduce the bias array into a bias value or a threshold may reduce the bias into a single value.

It should be understood that the AutoNDI data may be processed or reprocessed at a later time, for example, when bias data become available or to utilize new bias data or new equations and constants. Peak stresses for example, may be obtained from Riser analysis software that is typically calculated for every well and may be converted into a Riser string bias array. A Riser string design typically comprises of a sequence of Riser joint identification numbers. A Riser string design may be further validated by combining the previously stored Riser inspection data with its location in the string and the bias array.

AutoNDI System Considerations

The overall AutoNDI system must be feasible not only from the classification standpoint but also from the realization standpoint. In addition to the classification and minimum error, the system constraints also include, but are not limited to, cost, packaging, portability, reliability, and ease of use; all of which should be addressed in each step of the design. The system design preferably must assign initial resources to each level and should attempt to minimize or even eliminate resources whose overall contribution is negligible. This can be accomplished by converting certain features to bias and evaluating the resulting error.

Computer 10 preferably recognizes the imperfection by comparing the final array of identifiers 55, 56, 59 with a stored imperfection template database. Once an imperfection is recognized, computer 10 may verify the correctness of the recognition by further evaluating intermediate identifiers.

Occasionally, the imperfection recognition becomes unstable with the final array of identifiers toggling between two solutions on each iteration. For example, during the inspection of used production tubing, the recognition may bounce back and forth between a large crack and a small pit. Resolution of such instability may be achieved by utilizing intermediate identifiers, by utilizing the previous recognition value, or by always accepting the worst conclusion (typically referred to as pessimistic classification). However, AutoNDI instability may also be the outcome of improper backwards chaining or even faulty constraints. Slight increase in the coefficients of the backwards chained features may produce an output oscillation thus rapidly locating the problem feature and/or coefficients.

A conflict arises when the final array of identifiers points into two or more different MUI 9 conditions with equal probability. Again, resolution of such conflict may be achieved by utilizing intermediate identifiers, by utilizing the previous recognition value or by always accepting the worst conclusion. However, a definite solution may be obtained by eliminating features that the conclusions have invalidated and by reprocessing the signals under the new rules.

The AutoNDI is preferably designed to reason under certainty. However, it should also be capable of reasoning under uncertainty. For example, during the inspection of used production tubing of a gas well, rod wear is detected. Since there are no sucker rods in the gas well, the conclusion is that this is either used tubing that was previously utilized in a well with sucker rod or there is a failure in the AutoNDI. The AutoNDI could query previous inspection records 57 about the history of the tubing and specifically if it was new or used when initially installed in the well. The answer may be difficult to obtain, therefore a 50-50 chance should be accepted. A bias value may then be altered and the signal may be reprocessed under the new rules.

Alternate coefficients may be stored for use when certain failures are detected. For example, a wellhead pressure transmitter, also designated with the numeral 26 in FIG. 1, may fail. Upon detection of the failure, the alternate set of coefficients may be loaded for further use. It should be understood that even a simple bias may substitute for the failed transmitter.

An AutoNDI Application

Figure 3:
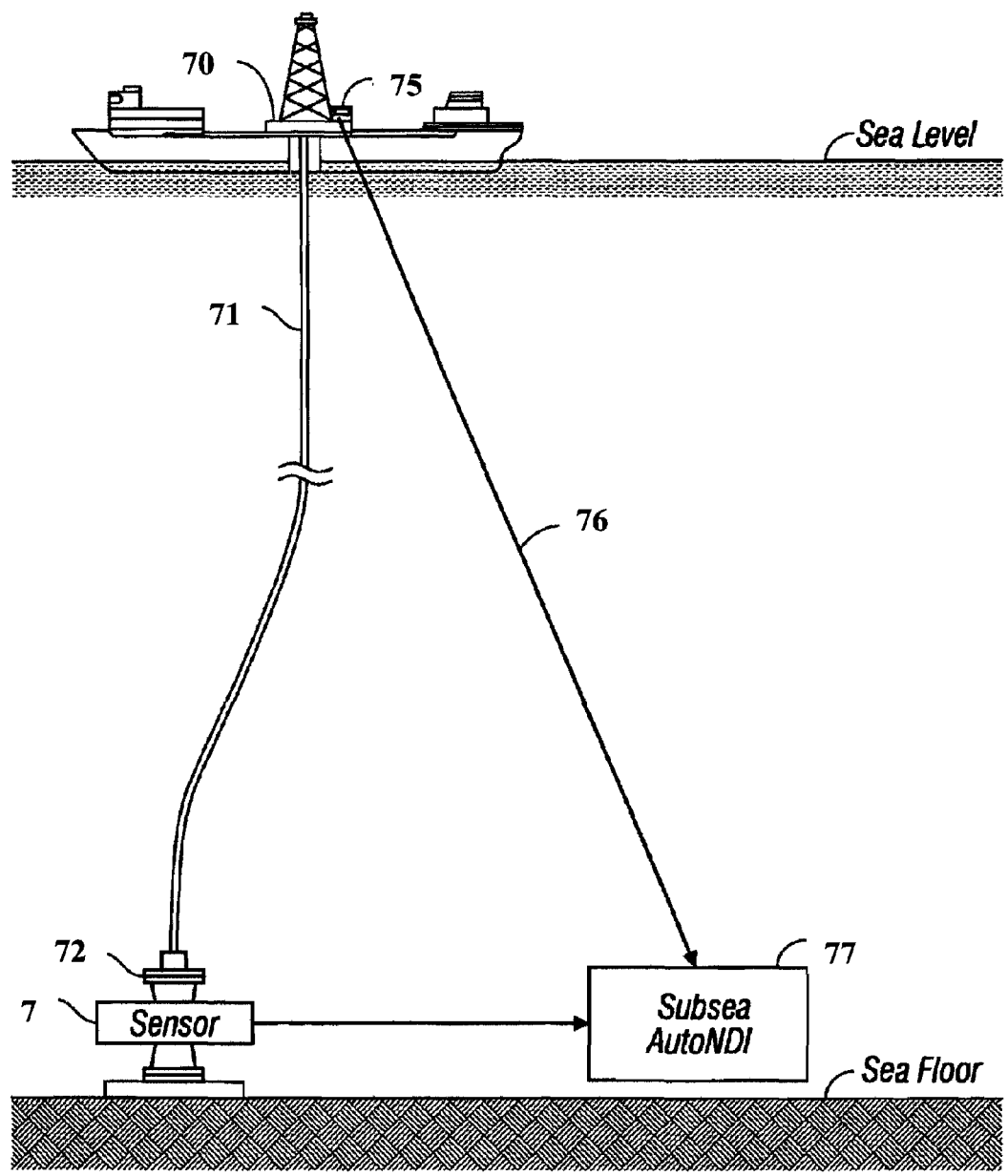
FIG. 3 illustrates a partially pictorial view using an autonomous non-destructive inspection system to locate well equipment according to the present invention.

As illustrated in FIG. 3, AutoNDI 75 may be deployed on the rig floor of rig 70 to inspect bottom hole assembly, casing, coiled tubing, drilling collars, drill pipe, tubing, other OCTG and well equipment during a trip, and preferably, during all trips, resulting in a constant-vigilance approach to safety. This constant-vigilance increases the detection probability of imperfections before they become flaws, or later, defects and reduces greatly the public, personnel, environment and equipment risk by monitoring the growth, shape, expansion, progress, migration and bridging of the imperfection families.

For example, a small hole in the OCTG coating may allow the well environment to corrode initially a very small OCTG area. This would most likely go unnoticed, but typically, it would propagate and expand underneath the coating. The resulting pits would also act as stress-concentrators under loading. Another example would be manufacturing errors and omissions or handling and transportation damage that may be the original cause of the small hole in the OCTG coating. Another benefit of the present invention is to minimize unnecessary handling of the material. An OCTG hard-spot would also act as a stress-concentrator under loading.

Eventually, the loading would give rise to cracks at the bottom of the pits or other stress-concentrators. Multiple studies have concluded that this damage accelerates much faster under dynamic loading in a corrosive environment and may lead to an early OCTG failure. As opposed to 1D-NDI, the aim of AutoNDI constant-vigilance is to detect imperfections early on to permit remediation before severe damage to the OCTG or a catastrophic failure that may affect the public, the personnel, the environment and other equipment including the rig 70.

Emergency Disconnect AutoNDI Application offshore drilling there may be a need for an emergency disconnect between a drilling rig 70 and the sea-floor wellhead. For example, due to inclement weather, a dynamically positioned rig 70 may no longer be able to maintain its position above the sea floor wellhead. Typically, such a disconnect is referred to as an Emergency Disconnect Sequence or EDS. A properly executed EDS allows the rig to move off location without damaging the subsea equipment and still maintaining control of the well.

In offshore drilling, the drill pipe with the bottom hole assembly is deployed inside Riser 71 and extends below the sea floor. A typical EDS mandates that the drill string is picked up and hung off in the subsea blow-out preventer (hereinafter referred to as "BOP") 72 pipe rams. The sequence typically starts by pulling some of the drill pipe out of the wellbore and then closing BOP pipe rams on what it is estimated to be the center of a drill pipe joint. The drill string is then slacked off slowly until the tool joint lands on the shoulder of the closed BOP pipe rams. This is typically indicated by a drop in the weight indicator.

Thus, it becomes necessary to estimate the location of a drill pipe tool joint in BOP 72 stack with a high degree of confidence otherwise the rubber goods of BOP 72 pipe rams may become damaged and significantly reduce their effectiveness to hold pressure. Knowing the exact location of the drill pipe tool joint or other equipment, such as the bottom hole assembly, is critical information as it reduces the likelihood for damage to BOP 72 pipe rams and further assures that the shear rams will attempt to close on the drill pipe body wall, not a tool joint, a drilling collar, drill pipe with increased hardness or any other well and drilling equipment that may obstruct a shear. It should be understood that the AutoNDI views a drill pipe tool joint, a bottom hole assembly and other well and drilling equipment as a length with an increase in at least one of wall thickness, hardness, composition, geometry, similar items and combinations of the above.

AutoNDI 75 may be used to locate well and drilling equipment such as, but not limited to a tool joint, in BOP 72 pipe and shear rams. During inspection, AutoNDI 75 monitors the OCTG length and the rig motion through sensors 24 and 26. Thus AutoNDI can calculate the location of each tool joint and other well and drilling equipment from the sea floor or BOP 72 and also correct for elongation, buoyancy, wave action etc.

However, it should be appreciated that other material combinations and circumstances may result in a wall thickness and geometry variation inside BOP 72 shear rams that may prevent the shear rams from operating. This condition cannot be detected by surface AutoNDI 75 but it can easily be detected by subsea AutoNDI 77 with at least one sensor 7 monitoring at least one BOP 72 ram. Subsea AutoNDI 77 would also detect other abnormal conditions and may raise an alarm that may prevent a catastrophe. Preferably, AutoNDI 75 and 77 may indicate on the rig floor shear/no-shear conditions with a green/red light. It should be noted that shear works best on drill pipe body-wall when the drill pipe is under tension and centered in BOP 72 rams. Sensor 26 could be monitoring the drill pipe tension and weight on the rig floor and subsea sensor 7 may also monitor the center/off-center of the drill pipe in BOP 72 in addition to detecting the drill pipe tool joint and other well equipment.

During a well blowout, broken pieces of drilling equipment may pass through sensor 7 of subsea AutoNDI 77 where they will be detected and raise one or more alarms. This may alert the rig crew of the abnormal condition before it reaches the surface. Another piece may be lodged inside BOP 72. This condition would also be detected by AutoNDI 77 and may be corrected by tripping out some drill pipe. In addition, during the blowout mayhem, there may be a moment were shear is possible, detected by AutoNDI 77, and a timely manual or automatic action may prevent the catastrophe altogether.

Due to the high operating pressures endured by the subsea stack, the drill pipe is typically surrounded by materials with a wall thickness in excess of one inch. Placing sensors inside the stack would appear to be the solution, however, this would expose the sensors to the action of the drilling fluids and the drill pipe, thus mandating armor around the sensors. Calculations would reveal that the armor would be of significant thickness itself and would require the redesign of subsea assemblies in order to accommodate the armored sensors and still maintain a desired ID clearance within the bore of the subsea stack.

External sensors can be fitted on existing stack components with minimal or no alteration. However, the exciter (6 in FIG. 1) for the external sensors (7 in FIG. 1) would have to have sufficient power for the excitation to penetrate through the significant wall thickness in order to detect the drill pipe tool joint, thus, the detection system would require high power. Both space and power are extremely limited and of high value on the sea floor and on the subsea stack. Thus, the use of active tool joint detection techniques, such as, but not limited to, electromagnetic, ultrasonic, and radiation would be cost prohibitive.

The present invention overcomes these problems by utilizing a very low power passive tool joint and other equipment detection technique that can be easily installed on new equipment as well as retrofitted on existing equipment. The locator requires an AutoNDI 75 unit on the surface in communication with a subsea AutoNDI 77. When the drill pipe is tripped into the well, surface AutoNDI 75 prepares the drill pipe for both tool joint location and the subsequent inspection. It should be noted that the distance between the sensors of AutoNDI 75 and subsea AutoNDI 77 can be accurately determined at the moment AutoNDI 77 detects the first drill pipe. When the drill pipe is tripped out of the well, surface AutoNDI 75 or both AutoNDI 75 and 77 may inspect the drill pipe. Both AutoNDI 75 and 77 locate the tool joints in the subsea stack; AutoNDI 75 through calculations and AutoNDI 77 through sensor 7. It should be understood that more than one subsea AutoNDI 77 may be deployed in order to increase the overall system reliability and availability.

The drill pipe, other OCTG or equipment is magnetized at the rig floor while it is tripped into the well. At least one passive sensor 7 is preferably mounted externally on a convenient BOP 72 component, thus the distances between the pipe rams and shear rams and the tool joint sensor is fixed and known to the driller and AutoNDI 75 and 77. It should be appreciated that a passive sensor may also be mounted internally to a subsea stack component. Active sensors may also be used, placing a higher power requirement on the system. It should be further appreciated that the sensor 7 can also be any other AutoNDI sensor. It should be further understood that more than one sensor configuration, each of which are known in the art, may be employed to increase the probability of the tool joint identification and to detect the lateral position of the drill pipe in the stack.

Subsea AutoNDI 77 is preferably connected to the surface with two wires 76 for both power and communication or through the mux. The surface AutoNDI 75, is preferably located on the rig floor of the rig 70 and would inform the driller when a tool joint is inside the subsea sensor 7 or inside the pipe rams or the shear rams. Subsea AutoNDI 77 may reduce the data into a single bit (a relay contact for example) that represents a shear/no-shear which can easily be transmitted to the surface through the mux or other communication means.

The tool joint identification signature is a function of the drill pipe dimensions and the location of the tool joint sensor. Thus, a training sequence would be required to tune the different identifier equations. The coefficients would preferably be stored onboard the subsea AutoNDI 77 and be selected through the power and communication link 76 or through the mux. Since the entire function of the subsea AutoNDI 77 is to detect a tool joint and other abnormal conditions, preferably it would utilize a sufficient number of identifier equations to increase the probability of detection.

Riser AutoNDI Application

In addition to marine drilling risers, Riser 71 also encompasses catenary risers, flexible risers and production risers. Risers provide a conduit for the transfer of materials, such as drilling and production fluids and gases, to and from the seafloor equipment, such as BOP 72, to surface floating platform 70. A Riser joint may comprise of a single or multiple tubes and are designed to withstand a range of operation Loads while submerged. It is reasonable therefore to expect that the applicable standards and recommended practices would discuss and set allowable stress limits and/or maximum allowable Loads. American Petroleum Institute (API) 16Q and 16F specify that the maximum stresses, as calculated by von Mises failure criterion, should not exceed 0.67 of Riser strength. It is important therefore to detect and recognize Riser Features that act as stress-concentrators to allow for the calculation of a maximum stress.

Correcting an Industry Dangerous Practice

It should also be noted that AutoNDI corrects a dangerous industry practice. Because of the 1D-NDI signal comingling and its limited dynamic range, Riser tubes fall well outside the inspection capabilities of 1D-NDI and therefore, inspection companies are not involved with the inspection of Risers. On the other hand, the primary concern of Riser manufacturers (herein referred to as "Riser-OEM") is to verify the compliance of the new tubes with the purchase order prior to assembling them into a new Riser. A limited manual 1D-NDI sampling (herein referred to as "Spot-Checks") is sufficient to verify compliance. Riser-OEM Spot-Checks comprise of a number of manual spot readings that typically cover less than 1% of Riser tube, again, due to the limitations of the available 1D-NDI technology. Typically, a Riser-OEM Spot-Check comprises of four (4) wall thickness readings around Riser 71 circumference every 2 to 5 feet resulting in less than 1% inspection coverage for wall thickness only.

However, this Riser-OEM Spot-Checks is inadequate and inappropriate for the inspection of used Risers where 100% inspection coverage is essential for the calculation of the maximum (peak) Riser stresses. It should also be noted that Riser-OEM Spot-Checks are inadequate and inappropriate for the inspection of all other new or used OCTG, like drill pipe. The simplicity of the Spot-Checks, the modest investment in tools and the lack of required certification and monitoring has encouraged many to enter the used Riser inspection market.

FIGS. 4, 5, and 6 detail Riser-OEM and others intrusive and destructive inspection process that exposes Riser 71 to handling, transportation, disassembly, reassembly and numerous other risks for a very expensive but insignificant (less than 1%) inspection coverage that cannot assure Riser 71 integrity and cannot be used for the calculation of Riser 71 maximum stresses.

It should be noted that for decades drill pipe and other used OCTG inspection mandates 100% inspection coverage by certified and monitored inspection companies using calibrated equipment. Again, Riser-OEM spot-checks do not meet the new or used drill pipe and other OCTG minimum inspection requirements. In offshore drilling, drill pipe is deployed inside Riser 71 Main Tube along with the drilling and well fluids. The irony of it all is that if the drill pipe breaks it would result in an inconvenience as Riser 71 will contain the fluids and gases, will protect the environment and limit any harmful consequences. If Riser 71 breaks, drilling and well fluids and gases would be released immediately to the environment with limited means to control the damage and the pollution. It should also be noted that gases may reach the surface underneath or very near the floating platform and may ignite, a familiar Gulf-of-Mexico scenario. In other words, 100% inspection coverage by a certified and monitored inspection company is mandated to prevent an inconvenience while 1% or less inspection coverage by anybody through an intrusive and destructive process is deemed adequate to prevent a disaster.

The deployment of the AutoNDI corrects this dangerous industry practice by providing 100% inspection coverage of the as-is where-is (horizontal or vertical) Riser 71 tubes, preferably onboard the rig 70; by recognizing Riser 71 Features with sufficient resolution to allow for the calculation of maximum Riser 71 stresses under loading and by only shipping to a maintenance/repair facility Risers 71 in need of maintenance or repair.

It may be seen from the preceding description that a novel autonomous inspection system and control has been provided. Although specific examples may have been described and disclosed, the invention of the instant application is considered to comprise and is intended to comprise any equivalent structure and may be constructed in many different ways to function and operate in the general manner as explained hereinbefore. Accordingly, it is noted that the embodiments described herein in detail for exemplary purposes are of course subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A constant-vigilance monitoring system comprising of:
   at least one computer with storage, data entry, and data readout;
   at least one subsea sensor secured to a subsea blowout preventer with an output in communication with said computer;
   software to analyze said output of said at least one subsea sensor to determine relative positions of tubular goods or broken drilling equipment in said blowout preventer;
   software to determine if rams of said blowout preventer are capable of shearing or sealing around said tubular goods at a particular time depending on said relative positions; and
   at least one processor to execute said software for said at least one computer to determine said relative positions and to determine if said rams are capable of shearing or sealing.

2. The constant-vigilance monitoring system of claim 1 further comprising:
   at least one surface sensor at a surface position with a second output in communication with said at least one computer, and software to detect a length of said tubular goods.

3. The system of claim 1, wherein said tubular goods comprises of at least one drill pipe.

4. The system of claim 1, wherein said tubular goods comprises of at least one casing.

5. The system of claim 1, wherein said tubular goods comprises of at least one tubing.

6. The system of claim 1, wherein said tubular goods comprises of coiled tubing.

7. The system of claim 1, wherein said tubular goods comprises of at least one pipeline.

8. The system of claim 1, wherein said tubular goods comprises of at least one bottom hole assembly.

9. The system of claim 1, further comprising said at least one computer is programmed to utilize identifier equations to analyze signals from said subsea sensor, and wherein said at least one computer is responsive to voice commands.

10. A constant-vigilance monitoring system comprising of:
    at least one computer with storage, data entry, and data readout;
    at least one subsea sensor secured to a subsea blowout preventer with an output in communication with said at least one computer;
    said at least one computer being programmed to analyze an output of said at least one subsea sensor to determine a geometry of tubular goods;
    said at least one computer being programmed to determine if rams of said subsea blowout preventer are capable of shearing or sealing around said tubular goods at a particular time utilizing said geometry of said tubular goods; and
    at least one processor to provide program execution for said at least one computer comprising said determination of said geometry and said determination if said rams are capable of shearing or sealing at said particular time.

11. The constant-vigilance monitoring system of claim 10 further comprising
    at least one surface sensor at a surface position with an output in communication with said at least one computer, and said at least one computer being programmed to detect a length of said tubular goods.

12. The constant-vigilance monitoring system of claim 11 further comprising
    said at least one computer being programmed to analyze said outputs of said surface sensor and said subsea sensor to determine if said subsea blowout preventer can be operated without encountering a tool joint.

13. The constant-vigilance monitoring system of claim 12 wherein said at least one computer being programmed to produce a shear-no shear signal.

14. The constant-vigilance monitoring system of claim 13 wherein said at least one surface sensor detects drill pipe weight, said at least one computer being further programmed to utilize said drill pipe weight for determining said shear-no shear signal.

15. The system of claim 10 wherein said at least computer is programmed to automatically operate said shear rams to shear said tubular goods after said at least one computer determines that said shear rams are capable of shearing said tubular goods.

16. The system of claim 10, further comprising a surface mounted exciter operable to magnetize said tubular goods, and wherein said subsea sensor is a passive sensor.

17. The system of claim 10, wherein said subsea sensor is mounted internally of said subsea blowout preventer.

18. The system of claim 10, wherein said subsea sensor is mounted externally to said subsea blowout preventer.

19. The system of claim 10, further comprising a surface automatic nondestructive inspection module comprising of said at least one computer connected to at least one surface sensor and an exciter operable to magnetize said tubular goods.

20. The system of claim 10, wherein said at least one computer further comprising a surface computer and a subsea computer, and further comprising an electrical interconnection between said surface computer and said subsea computer.

21. The system of claim 20, wherein said electrical interconnection comprises at least two wires for power and communication.

22. The system of claim 21, wherein said subsea computer is programmed to utilize identifier equations to analyze signals from said subsea sensor.

23. The system of claim 22 wherein said identifier equations comprise coefficients stored in said subsea computer.

24. The system of claim 23 wherein said subsea sensor comprises a magnetic sensor responsive to said magnetized tubular goods.

25. The system of claim 22, wherein said surface computer is programmed to utilize identifier equations to determine a geometry of said tubular goods.

26. The system of claim 10, wherein said tubular goods comprises of at least one drill pipe.

27. The system of claim 10, wherein said tubular goods comprises of at least one casing.

28. The system of claim 10, wherein said tubular goods comprises of at least one tubing.

29. The system of claim 10, wherein said tubular goods comprises of at least one coiled tubing.

30. The system of claim 10, wherein said tubular goods comprises of at least one pipeline.

31. The system of claim 10, wherein said tubular goods comprises of at least one bottom hole assembly.

32. A constant-vigilance monitoring method comprising of:
providing at least one computer with storage, data entry, and data readout;
providing a subsea sensor for a blowout preventer in communication with said at least one computer;
providing said at least one computer is programmed to analyze an output of said subsea sensor to determine relative positions of tubular goods or broken drilling equipment in said blowout preventer of said tubular goods;
providing said at least one computer is programmed to determine if rams of said blowout preventer are capable of shearing or sealing around said tubular goods at a particular time depending on said relative positions; and
providing at least one processor to provide program execution for said at least one computer comprising said determination of said relative positions and said determination if said rams are capable of shearing or sealing at said particular time.

33. The method of claim 32 further comprising providing at least one surface sensor at a surface position with a second output in communication with said at least one computer, and providing said at least one computer is programmed to detect a length of said tubular goods.

34. The method of claim 32, further comprising of providing that said at least computer is programmed to automatically operate said shear rams to shear said tubular goods after said at least one computer determines that said rams are capable of shearing said tubular goods.

35. The method of claim 32, further comprising providing that said at least one computer comprises a surface computer and a subsea computer.

36. The method of claim 32, wherein said tubular goods comprises of at least one drill pipe.

37. The method of claim 32, wherein said tubular goods comprises of at least one casing.

38. The method of claim 32, wherein said tubular goods comprises of at least one tubing.

39. The method of claim 32, wherein said tubular goods comprises of coiled tubing.

40. The method of claim 32, wherein said tubular goods comprises of at least one pipeline.

41. The method of claim 32, wherein said tubular goods comprises of at least one bottom hole assembly.

42. A constant-vigilance monitoring method comprising of:
providing at least one computer with storage, data entry, and data readout;
providing at least one subsea sensor secured to a subsea blowout preventer with an output in communication with said at least one computer;
providing said at least one computer is programmed to analyze an output of said at least one subsea sensor to determine a geometry of tubular goods;
providing said at least one computer is programmed to determine if rams of said subsea blowout preventer are capable of shearing or sealing around said tubular goods at a particular time utilizing said geometry of said tubular goods; and
providing at least one processor for said at least one computer for program execution comprising said determination of said geometry and said determination if said rams are capable of shearing or sealing at said particular time.

43. The method of claim 42 further comprising
providing at least one surface sensor at a surface position with an output in communication with said at least one computer, and providing that said at least one computer is programmed to detect a length of said tubular goods.

44. The method of claim 43, further comprising of providing
that said at least one computer is programmed to analyze said outputs of said surface sensor and said subsea sensor to determine if said subsea blowout preventer can be operated without encountering a tool joint.

45. The method of claim 44 further comprising providing that said at least one computer is programmed to produce a shear-no shear signal.

46. The method of claim 45 further comprising providing that said at least one surface sensor detects drill pipe weight, and providing that said at least one computer is further programmed to utilize said drill pipe weight for determining said shear-no shear signal.

47. The method of claim 46, further comprising providing that said surface computer is programmed to utilize identifier equations to detect tool joints in said tubular goods.

48. The method of claim 42, wherein said tubular goods comprises of at least one drill pipe.

49. The method of claim 42, wherein said tubular goods comprises of at least one casing.

50. The method of claim 42, wherein said tubular goods comprises of at least one tubing.

51. The method of claim 42, wherein said tubular goods comprises coiled tubing.

52. The method of claim 42, wherein said tubular goods comprises of at least one pipeline.

53. The method of claim 42, wherein said tubular goods comprises of at least one bottom hole assembly.

54. The method of claim 42, further comprising of providing that said at least computer is programmed to automatically operate said rams to shear said tubular goods after said at least one computer determines that said rams are capable of shearing said tubular goods.

55. The method of claim 42, further comprising of providing a surface mounted exciter operable to magnetize said tubular goods, and wherein said subsea sensor is a passive sensor responsive to magnetized tubular goods.

56. The method of claim 42, further comprising providing that said at least one computer utilizes identifier equations to determine said geometry of said tubular goods.

57. The method of claim 42, further comprising of providing that said subsea sensor is mounted internally of said subsea blowout preventer.

58. The method of claim 42, further comprising providing a surface automatic nondestructive inspection module comprising of said at least one computer connected to at least one surface sensor and magnetizing said tubular goods.

59. The method of claim 42, further comprising providing that said at least one computer comprises a surface computer and a subsea computer, and further comprising providing an electrical interconnection between said surface computer and said subsea computer.

60. The method of claim 59, further comprising providing that said electrical interconnection comprises at least two wires for power and communication.

61. The method of claim 60, further comprising providing that said subsea computer is programmed to utilize identifier equations to analyze signals from said subsea sensor.

62. The method of claim 61, further comprising providing that said identifier equations comprise coefficients.

63. The method of claim 62, further comprising providing that said coefficients are selectable for different sizes of said tubular goods utilizing said electrical interconnection.

* * * * *